United States Patent
Mellars

(10) Patent No.: US 9,778,275 B2
(45) Date of Patent: Oct. 3, 2017

(54) CONFIRMED PLACEMENT OF SAMPLE TUBES IN A SERVO DRIVEN AUTOMATION SYSTEM USING TRAJECTORY DEVIATION

(71) Applicant: Siemens Healthcare Diagnostics Inc., Tarrytown, NY (US)

(72) Inventor: Colin Mellars, Dover, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/034,729

(22) PCT Filed: Oct. 30, 2014

(86) PCT No.: PCT/US2014/063241
§ 371 (c)(1),
(2) Date: May 5, 2016

(87) PCT Pub. No.: WO2015/069547
PCT Pub. Date: May 14, 2015

(65) Prior Publication Data
US 2016/0299161 A1 Oct. 13, 2016

Related U.S. Application Data

(60) Provisional application No. 61/900,656, filed on Nov. 6, 2013.

(51) Int. Cl.
*G01N 35/04* (2006.01)
*G01N 35/00* (2006.01)
(Continued)

(52) U.S. Cl.
CPC ......... *G01N 35/04* (2013.01); *G01N 35/0099* (2013.01); *G01N 35/026* (2013.01);
(Continued)

(58) Field of Classification Search
CPC ............ G01N 35/0099; G01N 35/026; G01N 35/0491; G01N 2035/0465; G01N 35/04
See application file for complete search history.

(56) References Cited

U.S. PATENT DOCUMENTS 4,356,439 A 10/1982 Mott et al.
5,096,670 A * 3/1992 Harris ................. G01N 35/028
356/244
(Continued)

FOREIGN PATENT DOCUMENTS

DE 102006022817 A1 11/2007
DE 10 2011 006679 A1 9/2012
(Continued)

OTHER PUBLICATIONS

Extended EP Search Report dated Oct. 21, 2016 of corresponding European Application No. 14859969.9, 5 Pages.
(Continued)

*Primary Examiner* — Thomas Randazzo

(57) ABSTRACT

A system for placing sample tubes into tube receptacles includes a sample handling device that includes an electrical signal, relating to an operating condition, such as a position error, a tube receptacle, and a processor configured to control the sample handling device in response to the electrical signal. The processor observes the operating condition for signal artifacts that indicate that a sample vessel being placed has encountered a holding spring and subsequently the bottom of the tube receptacle. The processor provides substantially real-time control of the motion of the sample handling device in response.

22 Claims, 5 Drawing Sheets

(51) Int. Cl.
    *G01N 35/02*     (2006.01)
    *B25J 9/16*     (2006.01)

(52) U.S. Cl.
    CPC ..... *B25J 9/1687* (2013.01); *G01N 2035/0475* (2013.01); *G01N 2035/0491* (2013.01); *G01N 2035/0494* (2013.01); *G05B 2219/37002* (2013.01); *G05B 2219/45092* (2013.01)

(56) References Cited

U.S. PATENT DOCUMENTS

| | | | |
|---|---|---|---|
| 5,986,417 A * | 11/1999 | Nicolai | H02P 25/14 |
| | | | 318/245 |
| 6,089,101 A | 7/2000 | Ishii et al. | |
| 6,429,016 B1 | 8/2002 | McNeil | |
| 6,463,720 B1 | 10/2002 | Cherney et al. | |
| 6,544,799 B1 | 4/2003 | Lewis et al. | |
| 7,128,874 B2 | 10/2006 | Kittock et al. | |
| 7,130,718 B2 | 10/2006 | Gunnarsson et al. | |
| 7,249,529 B2 * | 7/2007 | Massaro | G01N 35/0099 |
| | | | 73/863.31 |
| 7,262,575 B2 | 8/2007 | Kircanski et al. | |
| 7,450,127 B2 | 11/2008 | Hong et al. | |
| 7,578,978 B2 | 8/2009 | Justin et al. | |
| 8,916,097 B2 * | 12/2014 | Stein | G01N 35/0092 |
| | | | 422/62 |
| 2002/0146347 A1 | 10/2002 | McNeil | |
| 2010/0129789 A1 | 5/2010 | Self et al. | |
| 2012/0134769 A1 * | 5/2012 | Friedman | G01N 35/0099 |
| | | | 414/751.1 |
| 2012/0140230 A1 * | 6/2012 | Miller | G01N 15/042 |
| | | | 356/441 |
| 2012/0178170 A1 | 7/2012 | Van Praet | |
| 2012/0330463 A1 | 12/2012 | Schreiber et al. | |
| 2013/0138236 A1 | 5/2013 | Nagaoka | |
| 2015/0118756 A1 * | 4/2015 | Pollack | G01N 35/0092 |
| | | | 436/43 |
| 2015/0298321 A1 * | 10/2015 | Gross | B65G 11/023 |
| | | | 422/67 |
| 2016/0025756 A1 * | 1/2016 | Pollack | G01N 35/04 |
| | | | 436/47 |

FOREIGN PATENT DOCUMENTS

| | | | | |
|---|---|---|---|---|
| WO | | 2012/018993 A1 | 2/2012 | |
| WO | | 2013/116638 A1 | 8/2013 | |
| WO | | 2013/151920 A1 | 10/2013 | |
| WO | WO 2013151920 A1 * | 10/2013 | | ......... G01N 35/0092 |

OTHER PUBLICATIONS

PCT International Search Report and Written Opinion dated Feb. 18, 2015 (10 Pages).

* cited by examiner

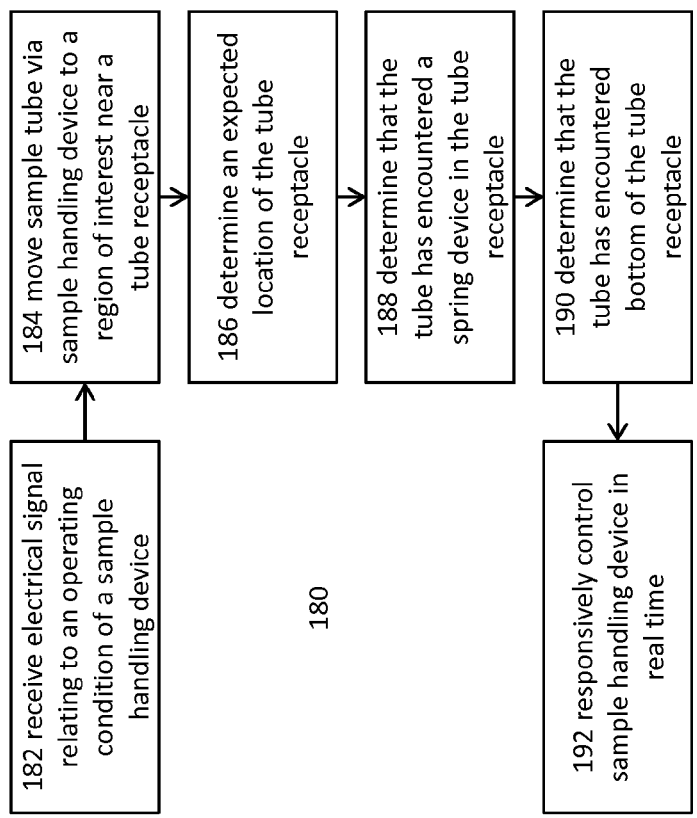

CONFIRMED PLACEMENT OF SAMPLE TUBES IN A SERVO DRIVEN AUTOMATION SYSTEM USING TRAJECTORY DEVIATION

CROSS-REFERENCE TO RELATED APPLICATIONS

This application claims priority to U.S. provisional application Ser. No. 61/900,656 filed Nov. 6, 2013, which is incorporated herein by reference in its entirety.

TECHNOLOGY FIELD

The present invention relates generally to automated systems for placing sample vessels into receptacles, and more particularly to utilizing condition information to confirm proper placement of sample vessels.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) into which tubes or vials containing patient samples have been loaded. Because of the variety of assays needed in a modern IVD lab, and the volume of testing necessary to operate a lab, multiple analyzers are often employed in a single lab. Within analyzers, there may be multiple stations used for preparation and analysis tasks. Accordingly, fluid samples are often carried in sample vessels, such as tubes, that are placed into carriers or trays throughout the laboratory system, manually or as part of an automation system.

During the handling of samples, tubes must routinely be removed from and placed into slots in these carriers and trays. Due to the volume at which samples need to be processed in a typical IVD environment, the task of handling sample vessels, to insert and remove these tubes from tube slots in trays and carriers, is handled by sample handling robot arms. These sample handling arms are generally automated and must detect the location of a sample slot and need to place a sample into the slot without damaging the sample.

Currently in laboratory automation there are a couple of approaches for detecting whether a test tube or sample tube has been firmly placed where it should be (e.g., inside of a holder/tube slot). Most laboratory automation systems use some type of spring-holder. The spring(s) can center a tube in the slot or press the tube to a side in a cavity that defines the tube slot. These tube holders could be part of pucks/carriers, part of trays, or located elsewhere in the instrument.

Fundamentally, most of the sample-handling robot arm systems and pick and place devices are stepper-motor-based systems. A couple of techniques are used to ensure placement without breaking the sample tube. A sensing unit can include a spring sensor, allowing mechanical detection and some compliance. Generally these sensors are built into the robot arm, because the trays and carriers are generally passive devices. When the tube is pushed down, the tube causes a certain deflection in the spring, and it triggers a sensor that identifies that the tube has compressed the spring by some predetermined amount. This amount can indicate that the sample handler has successfully seated the tube, and the automated system can then take action. However, this is an indirect measurement. All the system can tell is that it pushed a sample tube against something that applied enough force to trigger the sensor. Accordingly, mechanical errors could also trigger such a sensor.

A second approach is to keep everything in the sample handling system at effectively the same height, allowing the tube to be moved around with respect to a plane. If you assume little or no manufacturing deviation, variations in height can be fairly minimal and inconsequential. In these systems, a handling device can be taught or programmed to move the tube in an open loop fashion with respect to the plane, monitoring the x-y-z coordinates of the handling device. Because these systems typically lack feedback from sensors in tube slots, their operation assumes that moving a tube to a given location results in proper placement. It can be difficult to determine if positions have drifted, which can affect performance. These systems are often servo motor based.

Servo-based systems can generally move much faster than stepper motor systems. However, servos typically encounter problems when relying on mechanical crash/crush sensors. Because servo-based systems tend to move much faster than stepper-based systems, sensors may only alert the system of an error after a tube has collided with a tube holder. Accordingly, servo-based systems tend to be limited to open loop, position-based placement systems.

Accordingly, there are two general options for confirming to placement in the prior art. One is a closed loop system where a contact sensor on the arm or in the tube receptacle confirms contact between a tube and a tube slot. This would be typically used with a pick-n-place device or a robot arm that is stepper motor driven. Typically the systems using a closed loop move much slower than servo-based systems, because the lag between detection and halting. The additional time needed for processing mechanical sensor feedback generally necessitates slower point-to-point motion.

The second option is to use conventional distance/position detection means, such as encoding, to determine the position of the end effectors on the robot arm. This type of system would be termed an open loop system because there is no sensory feedback. Such systems can be useful for stepper systems or servo based robot arms or pick and place devices.

Existing systems may have certain drawbacks. Sensor-based closed-loop systems often have extra mass for the sensor unit on the arm. If you have these extra sensors, systems need bigger robots and more power in that to move them around to do their function. Systems end up adding more mass and over designing to compensate for sensors on the robot arm. This can also create larger power supply demand. There may more cabling, requiring bigger e-chains (a flexible chain that keeps the cables constrained in a moving device). Bigger e-chains means more resistance, more resistance means a higher power device which requires a larger power supply, etc.

Furthermore, stepper-based closed-loop systems tend to be fairly expensive. The individual sensing packages carry an increased cost, which includes the sensors and the auxiliary hardware and increased cost to build more robust mechanisms to support the sensors.

One drawback with conventional open-loop systems is that the system does not actually know where the tube is. If a device slips and the system doesn't detect it, it may mis-approximate where it is actually moving tubes. In an extreme example a system could completely miss an intended position by a wide margin, perhaps causing a sample tube to fall over, spill, or break. Such an error can be catastrophic in an IVD system as it can spread contamination to other systems and samples. Another error may occur where a tube is mis-positioned by a small amount, such that the tube sticks up higher than expected when it leaves the sample handling station. The tube top can then later encounter another mechanism in the automation system, crashing and breaking the test tube which can cause a sample splash or spill. This can lead to cross-contamination of a large area depending on the size of the device and the speed by which samples move. As long as open loop systems work as expected, they tend to work well, but can have catastrophic problems due to slight changes.

SUMMARY

Embodiments of the present invention address and overcome one or more of the above shortcomings and drawbacks by providing methods and systems to confirm placement of sample vessels in tube receptacles utilizing signals that may be used for other purposes, such as position error signals or observing motor load/current. The system can observe these signals to identify behaviors that can confirm proper placement or indicate that an error has occurred, allowing real-time control over placement of sample tubes without requiring tactile sensors used in conventional closed-loop placement systems.

In one aspect, embodiments of the present invention are directed to a system for placing sample tubes into tube receptacles, which includes a sample handling device configured to position a sample tube and to provide at least one electrical signal relating to an operating condition of the sample handling device and at least one tube receptacle configured to receive the sample tube from the sample handling device. The tube receptacle includes a bottom and at least one spring device configured to apply a holding force to the sample tube when placed in the tube receptacle. At least one processor is configured to control the sample handling device and to receive the electrical signal, and is further configured to determine an expected location of the tube receptacle, determine, during placement of the sample tube, from the at least one electrical signal, that the tube has encountered the spring device, and subsequently determine from the at least one electrical signal that the tube has encountered the bottom of the tube receptacle, to verify proper placement of the sample tube. The processor is further configured to control the motion of the sample handling device in substantially real time, in response to these determination steps.

In some embodiments, the sample handling device includes at least one servo motor. In some embodiments, the at least one electrical signal indicates a deviation of at least one of an acceleration, a velocity, and a position, from an expected trajectory of the sample handling device. In some embodiments, the sample handling device includes at least one motor and the at least one electrical signal relates to a load experienced by the motor. In some embodiments, the sample handling device comprises a robot arm.

Furthermore, in some embodiments, the tube receptacle is part of a tray for carrying multiple sample tubes. In some embodiments, the tube receptacle is part of a carrier configured to move around an automation track in an analyzer. In some embodiments, a controller is configured to utilize the at least one electrical signal to determine an amount of power to use to maintain a trajectory of the sample handling device.

In one aspect, embodiments of the present invention are directed to a placement device for use in an IVD environment, where the device includes a sample handling device configured to position a sample tube and to provide at least one electrical signal relating to an operating condition of the sample handling device and at least one processor configured to control the sample handling device and receive the at least one electrical signal. The processor is configured to determine an expected location of a tube receptacle, determine, during placement of the sample tube, from the at least one electrical signal, that the tube has encountered a spring device in the tube receptacle, and subsequently determine from the at least one electrical signal that the tube has encountered a bottom of the tube receptacle, to verify proper placement of the sample tube in the tube receptacle. The processor is further configured to control the motion of the sample handling device in substantially real time, in response to the determination steps.

In some embodiments, the sample handling device includes at least one servo motor. In some embodiments, the electrical signal indicates a deviation of at least one of an acceleration, a velocity, and a position, from an expected trajectory of the sample handling device. In some embodiments, the sample handling device includes at least one motor and the at least one electrical signal relates to a load experienced by the motor. In some embodiments, the sample handling device comprises a robot arm.

In some embodiments, a controller is configured to utilize the at least one electrical signal to determine an amount of power to use to maintain a trajectory of the sample handling device. In some embodiments, the processor further determines a region of interest that includes a portion of a trajectory of the sample tube that includes the expected location of the spring device and the bottom of the tube receptacle.

In one aspect, embodiments of the present invention are directed to a method of placing sample tubes into tube receptacles, which includes steps of receiving, at a processor, at least one electrical signal relating to an operating condition of a sample handling device, moving a sample tube via the sample handling device to a region of interest near a tube receptacle, and determining an expected location of the tube receptacle. Steps further include determining, during placement of the sample tube, from the at least one electrical signal, that the tube has encountered a spring device in the tube receptacle, and subsequently determining from the at least one electrical signal that the tube has encountered a bottom of the tube receptacle, to verify proper placement of the sample tube in the tube receptacle. The steps also include controlling the motion of the sample handling device in substantially real time, in response to the determination steps.

In some embodiments, the sample handling device includes at least one servo motor. In some embodiments, the electrical signal indicates a deviation of at least one of an acceleration, a velocity, or a position, from an expected trajectory of the sample handling device. In some embodiments, the sample handling device includes at least one motor and the at least one electrical signal relates to a load experienced by the motor.

In some embodiments, the one tube receptacle is part of a tray for carrying multiple sample tubes. In some embodiments, the tube receptacle is part of a carrier configured to move around an automation track in an analyzer. In some embodiments, the step of moving the sample tube includes utilizing the at least one electrical signal to determine an amount of power to use to maintain a trajectory of the sample handling device.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 6 is a flow chart of an exemplary method for controlling motion of a sample handling mechanism for use with some embodiments.

DETAILED DESCRIPTION OF ILLUSTRATIVE EMBODIMENTS

Figure 1:
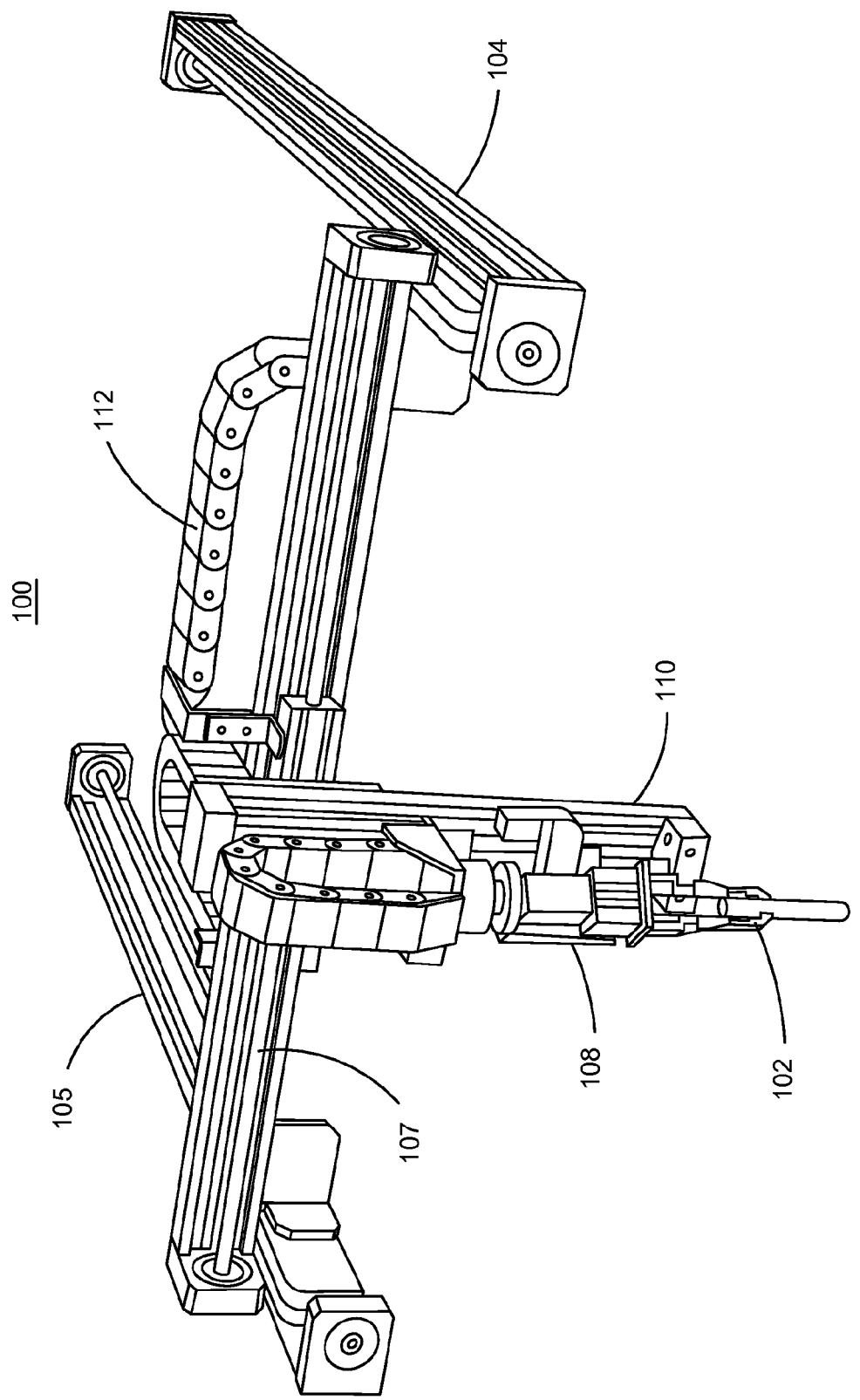
FIG. 1 is a perspective view of an exemplary sample handler for use with some embodiments.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment. A processor should be understood as a hardware device.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

Embodiments utilize signals related to motion profile error or motor load within a sample handling instrument to provide additional information to confirm proper placement of sample vessels. This may be particularly useful for improving performance of open loop systems by providing confirmation that the system is behaving properly before catastrophic failures occur. In some embodiments, these features may also be utilized in closed-loop systems.

Some embodiments take advantage of the speed of servo systems, while allowing the reliability of closed-loop systems. One way to reap this benefit is to utilize information about the state of a servo motor. This state information can include motor load, positional error, or other information that can indicate that a robot arm has encountered resistance. The signal used in embodiments can be existing signals already used by the control system that is driving the sample handling system. This can include a position error signal in the placement axis of a robot arm. If the placement axis (e.g. Z axis) is a rigid axis, (for most conventional cases, a vertical axis) such that the end effector are rigidly coupled to a motor that drives the end effectors up and down the axis, a controller can use a positional error signal to determine if the end effectors have encountered resistance.

It should be understood that when moving the robot arm in a large open space, ideally the controller attempts to move the end effector to be a certain position, and the effectors will lag in position by some amount based on the other control parameters in the control loop that's controlling it. When moving in open space, errors, such as those due to inertia, can largely be ignored when confirming placement, because the effectors are not near a position that should have a tube slot. When placing a tube, a controller keep track geometrically of where the tube and end effectors are relative to known objects, such as tube slots of trays or carriers. The system can define a region of interest in the geometry where the tube is expected to interact with a tube holder. The start of region of interest can be a predetermined height off set above where the effectors should place the tube. Above this region of interest, one would expect the end effector load and positional error signal to be very small and largely related to inertia and deflections due to normal load conditions. Using positional encoding or accumulating data from an accelerometer, or any other conventional means that would be apparent to a person of ordinary skill in the art, can determine approximately when the end effectors enter this region of interest. For most servo-based systems, positional information will readily be available to the controller.

When the system begins tube placement activity, the tube and the end effector will first the spring device is in the tube holder that is going to restrain to the sample tube within the tube slot. Depending on how sensitive the sample handling hardware is, encountering this spring will result in some tracking error, because it resists the motion of the sample tube, and thereby the end effectors. When moving with certain power from the motor controller, encountering the spring causes a change in resistance. Where the end effectors are at and where the controller wants them to be become two different values until the closed loop motor control system compensates for it. Servo systems are typically driven using a closed loop motor control system that dictates the power sent to the motor as part of a motion profile. It is said to be closed loop because feedback is necessary to drive the servo motor and ensure that a motion profile is being followed. It allows the motor driver to send more current to the motor to overcome resistance. It should be appreciated that the term closed loop with respect to servo motor control systems is different than the term is used to describe confirming placement of a tube by mechanical switch sensor, such as used in stepper motor-controlled placement systems. For example a closed-loop servo system may observe position encoding to determine that additional motor torque is needed to follow a requested motion profile.

A motor controller uses feedback from position sensors/encoding to reduce positional error to zero by adding more torque to the motor so that the end effectors can be moved in accordance with their expected motion profile, even when resistance is encountered. By observing the motion/position error encountered by the motor controller or the resulting current or torque output that the motor controller uses to overcome the error, a controller can also determine information about the environment around the end effectors without additional sensors. Position, velocity, or acceleration error from the expected profile, or increased torque requirements from expected, can indicate that a tube being held by the end effectors has encountered resistance. If this condition occurs in a region of interest, the controller can use this information to confirm that the tube has encountered the mechanism of the tube holder.

By observing the details of the error signal (e.g. motion or position error or increased current/load on the motor to adhere to the motion profile) a processor or controller can determine precise details about how the tube is interacting with the tube holder mechanism in a tube slot. For example, a slow rise in the error signal can indicate that the bottom of the tube has contacted a spring mechanism, which resists the insertion of the tube, but remains compliant. When the sample tube hits the bottom, the error signal will generally behave as an asymptotic deviation against the position below that floor. This is because the tube cannot physically reach the intended position below the floor of the tube holder and it effectively hits a mechanical barrier. A controller can use derivatives of the error signal look at the slopes to identify this asymptotic limit and stop driving the servo motor further to prevent damage to the sample vessel or to prevent improper placement of the sample.

A controller can be programmed to stop the motor before a predetermined threshold of motor torque has occurred, such that the effectors do not exceed a crush force of the tube and confirm placement has occurred. By checking the error signal to confirm that the spring has been encountered within the region of interest and then that the bottom has been encountered, placement can be confirmed. Observing the profile of the error signals within the region of interest can also confirm that the placement occurred as expected or that there was some anomaly in the placement.

From error signal profile that indicates the presence of the spring and the presence of the bottom, a processor can calculate the distance the arm has traveled, by considering time and velocity observed. From the geometry of the system, the depth of these carriers should be effectively constant. The processor can do a comparison to verify that the arm traveled the amount of depth expected, within a reasonably expected error of margin. The algorithm of the processor can then be confident that the arm placed the tube in the carrier and the tube did not extend too far. Otherwise, the processor can identify an error condition and the station can delay release of the tube and present the error to an operator or mitigate the error manually.

Several embodiments utilize the available information from the control system and the repeatable geometric parameters of the system to accomplish equivalent reliability of stepper-based/closed-system placement systems without the need for extra sensors. Effectively, the previously open-loop (with respect to confirmed placement) servo-system behaves in a closed loop condition using the motor load information so that it eliminates the open loop condition where there is no confirmation of placement. This may allow the system to be faster, smaller, lighter, cheaper, etc., allowing cheaper servo motors to quickly move samples outside the region of interest (e.g. acting in an open loop condition outside the region of interest) and then to behave similar to stepper motor-based systems with closed-loop confirmed placement.

FIG. 1 shows and exemplary sample handler 100 for use with some embodiments. In this example, a robot arm has end effectors 102 for engaging a sample tube. Dual Y-axis rails 104 and 105 allow travel of an X-axis rail 107 to position the robot arm and the end-effectors within the horizontal X-Y coordinate system. Travel along the Y-axis rails 104 and 105 is accomplished by manipulating control signals to right and left linear motors to move the X-axis rail 107. Similarly, travel along the X-axis is accomplished by manipulating control signals to X-axis linear motor 107 to move the robot arm carriage 108. The carriage contains a vertical, Z-axis rail 110 that allows manipulation of the vertical placement of the end effectors 102. Manipulation along the Z-axis is accomplished using a linear motor. The Z-axis motor 110 can be manipulated in accordance with the features disclosed herein. In some embodiments, the Z-axis motor 110 is a servo motor. In some embodiments, the Z-axis motor 110 provides an error signal that can be used to confirm placement, as discussed throughout. Control signals can be carried via control lines 112, which can include cable carrier chains to organize wires. Control signals can include sensor or encoding signals that are sent to a hardware processor. The processor and controller hardware together execute software to send power signals to manipulate the motor sample handler 100.

Figure 2:
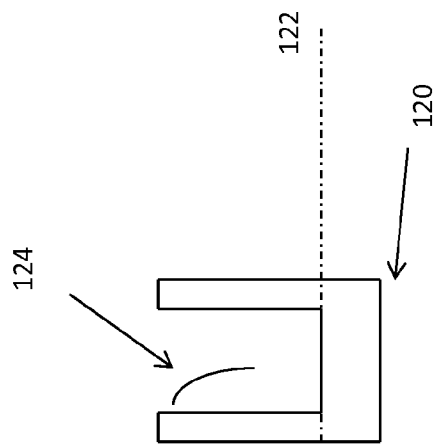
FIG. 2 is a cross sectional view of an exemplary sample tube receptacle for use with some embodiments.

FIG. 2 depicts a cross-sectional view of an exemplary sample slot/tube holder 120. Tube holder 120 can be part of an array of sample slots in a tray or part of a single sample slot that is part of a carrier or puck that allows individual samples to move about the automation system. Tube holder 120 includes a cavity with vertical sidewalls, which may be cylindrical or any other suitable shape, and a bottom 122. Bottom 122 provides a physical limitation that supports the bottom of a sample tube. Bottom 122 also prevents a sample tube from being pushed further into the cavity of tube holder 120. When a robot arm inserts a sample tube into the cavity of tube holder 120, bottom 122 provides a physical constraint to the motion. Placing too much downward force may cause a sample tube to break by impacting the bottom 122. One or more springs 124, which may include leaf springs or any other suitable spring, provides a holding force to secure the sample tube in the cavity of tube holder 120. In some embodiments, these may include self-centering springs, which allow the sample tube to be approximately centered in the cavity, allowing sample pipettors to more easily access samples held within the tube. Springs 124 may generally hold sample tube upright within the cavity.

An exemplary position error signal in a system work can work as follows. Software selects a trajectory for the end effectors to follow based on the intended task for placing a tube, the geometry of the station, and the location of the sample slot. A controller provides control signals to make the arm follow the trajectory based on a trajectory algorithm and feedback in the system (typically an encoder or a resolver used to determine robot arm position). Based on standard motor control algorithms and the desired trajectory, the controller commands the motor to move by giving the motor a certain amount of power. The control laws for a system can work by attempting to match the trajectory of the motor to the ideal trajectory. Due to basic physics and lag in the control system, the device will not perfectly track the ideal trajectory, and this can create an error signal. The error signal can be reflected in the feedback from the encoder vs the ideal position. The difference between the ideal trajectory and the observed position results in an error signal that can be used by a controller using conventional control means, such as a PID algorithm. This error signal is a delta error signal that is used to determine the power to be sent to the motor to direct the robot arm to follow the desired trajectory, accounting for the delta. It should be appreciated that this error signal is already part of conventional motor control schemes, and does not require additional sensors to utilize the concepts discussed herein with respect to embodiments.

Servo-based systems generally receive a desired trajectory to follow, which may be determined by an operator or algorithm. One or more motor controllers provides a power signal to motor components to make the end effectors of the robot arm move along the desired trajectory. Position encoding or other means for detecting position determines where in real space the end effector is. This measurement can be compared to the expected values based on the trajectory and used by a feedback control loop, such as a PID, which allows the power control signal to the motors to be adjusted accordingly. Motor control algorithms that are used in these typical schemes should be readily apparent to one of ordinary skill in the art. Generally, power signals and the control algorithm effectively compensate for errors, providing additional torque to motors when needed. In some embodiments, the error signal or the additional power needed to compensate for errors can be observed as an indication that the end effectors have encountered objects in the real world environment, without requiring additional sensors.

Embodiments utilize the principle that, by observing the error signal or torque requirements of one or more motors in the robot arm along with a model of the geometry of the environment, a software algorithm can effectively model certain conditions related to placing a sample tube in a tube holder. By utilizing this model of the conditions, software can effectively confirm placement in real time, while avoiding collisions or other catastrophic situations. For example, a controller may expect a tube to encounter a spring 50 mm from the bottom of a cavity. The controller can monitor for resistance at that location to confirm that the tube is being placed correctly and has encountered a centering spring. The location where resistance is first encountered can be used to establish baseline geometry between the arm and the cavity.

Moving another 50 mm, the control algorithm can expect to encounter resistance from the bottom of the cavity. If the arm only moves 18 mm and encounters unexpected resistance, this can indicate that something is in the way or that something is blocked and that there is a problem. The controller can flag this error and request that an operator come in and visually inspect and clear the hole. If there is a problem, an operator can come check the system or the arm can abort the placement, rather than releasing the tube to avoid problems. You can mitigate the failures without having to have all this extra external sensing just by analyzing the available mathematical signal that you already have in the control system.

Furthermore, if resistance is not encountered until the end effectors have traveled 45 mm, the control algorithm can stop the motor control from attempting to travel the full 50 mm, and assume that the real world bottom of the cavity is 5 mm from nominal. In this manner, the control algorithm may stop the tube from moving the full distance, avoiding crushing of the tube, while confirming proper placement of the tube. Optionally, software may note that for the given cavity the physical bottom was 5 mm from nominal. This information may be used to help calibrate and compensate for drift within the positional encoding, or to flag out-of-tolerance tube holders for future trajectory decisions.

Figure 3:
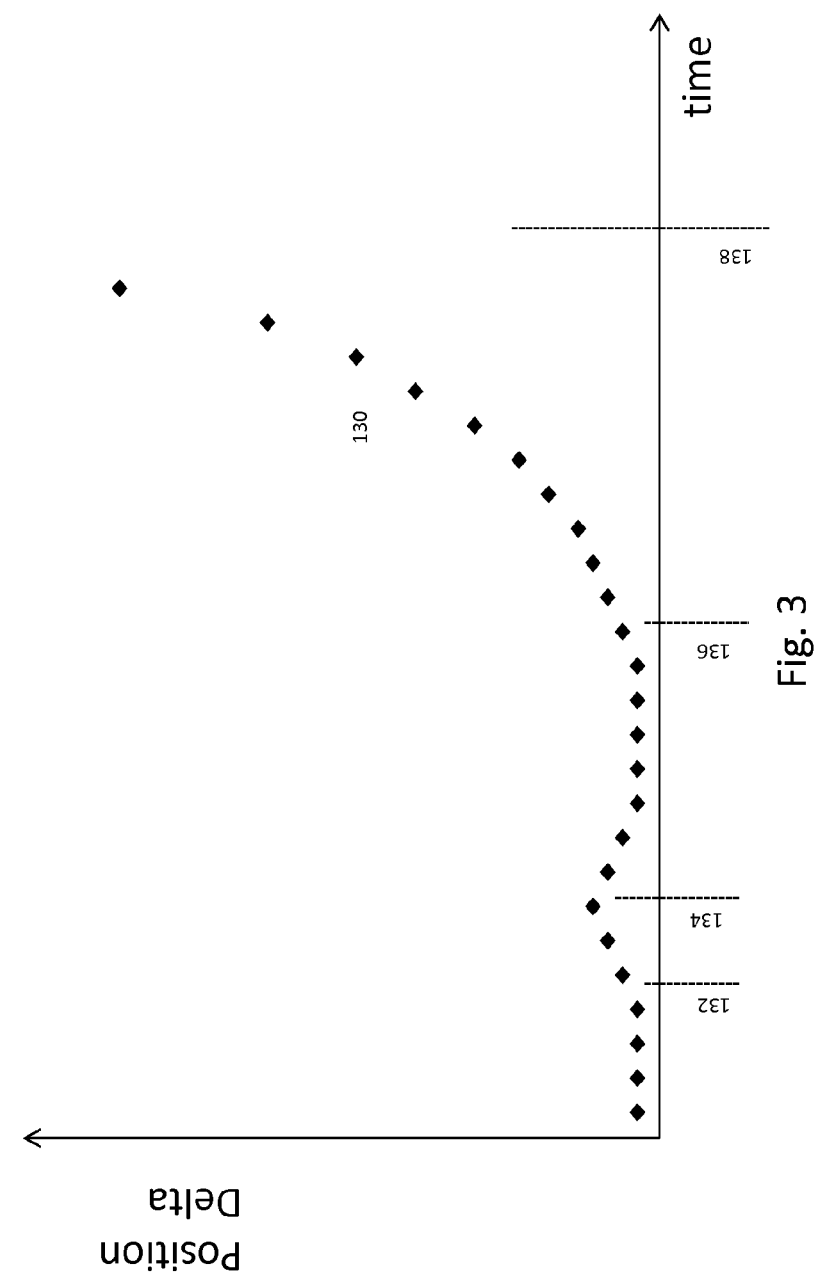
FIG. 3 is a graphical representation of an exemplary positional error curve that may be observed by a processor in accordance with some embodiments.
Figure 5:
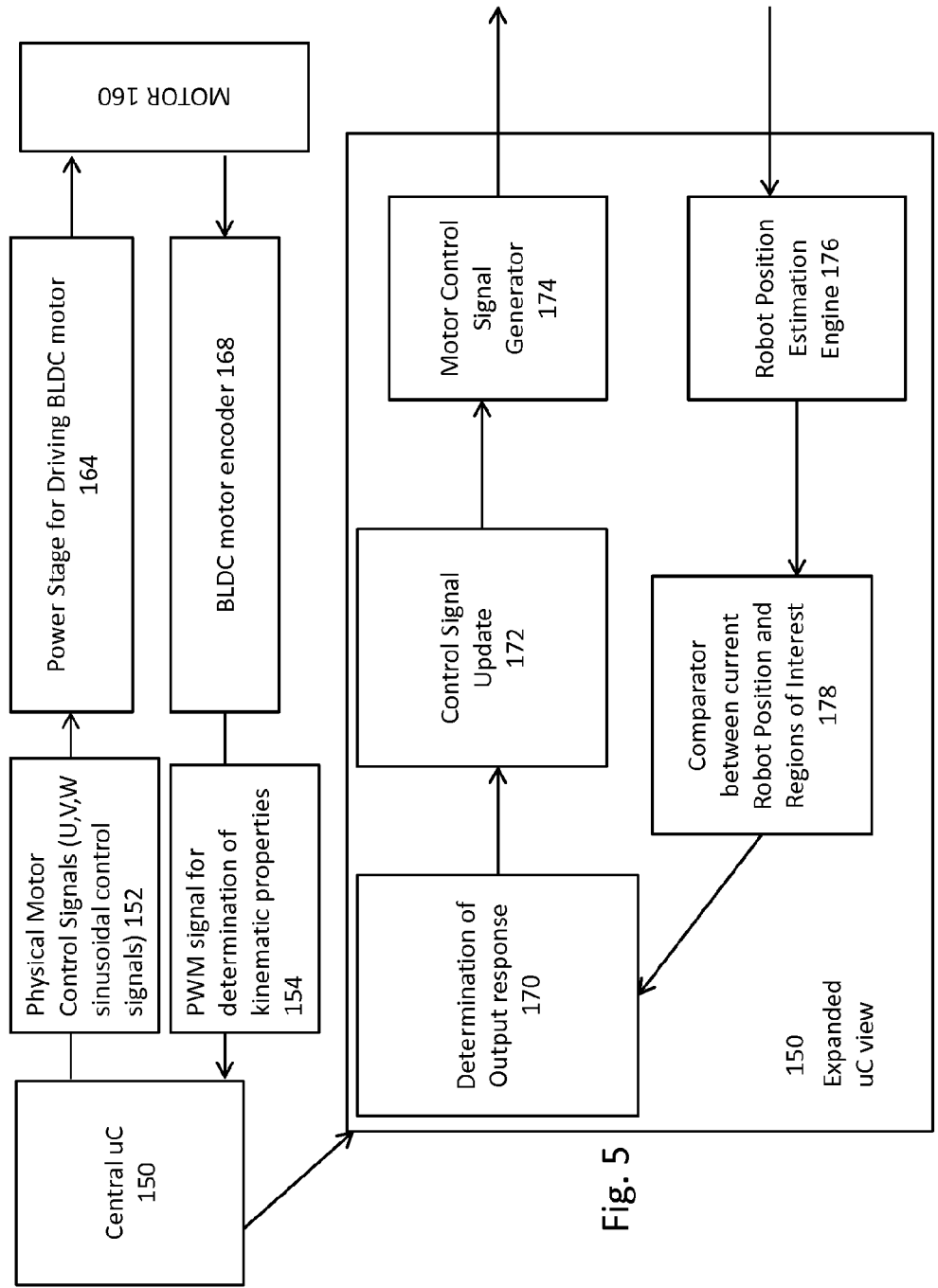
FIG. 5 is a system diagram of an exemplary control system for use with some embodiments.

FIG. 3 depicts an exemplary positional error curve that may be observed by a motor controller during normal placement of the sample tube into a tube holder. Curve 130 includes a plurality of samples of the error signal in the positional encoding. This example, the bottom of the sample tube is inserted into a tube holder. At time 132, the bottom of the tube encounters resistance due to deflection of a holding spring in the tube holder. This results in a gentle rise in the positional error, which requires additional torque to be applied by the motors to overcome the spring force. At time 134, the maximum positional deviation has occurred where the continued spring force causes a deceleration in the position of the end effectors, which was not accounted for in the original trajectory, because the trajectory did not account for the spring force. At the peak at time 134, the motor controller has sensed the slippage, and has sent additional current to the motor controlling the Z axis of the robot arm to overcome the positional discrepancy. After this peak, it can be seen that the positional error returns to zero as the frictional force due to the compressed spring is accounted for in the torque control signals sent to the Z axis motor. As time 136, the sample tube bottom encounters the bottom of the sample tube holder. For example, this may be 50 mm in space after the bottom of the tube encountered the spring and time 132. At time 136, the trajectory requirements caused torque signals to be continuously sent to the Z axis motor, but the tube has encountered the blockage of the bottom of the cavity. Accordingly, the positional error increases with time.

A typical motor control algorithm will respond by sending an increased current to the motors to compensate for the error. However, because the bottom of the cavity is solid, additional torque does not cause the sample tube to move, accordingly positional error increases greatly versus the expected value, based on the current sent to the motors. At time 138, it can be seen that the positional error results in an exponential or asymptotic behavior, such that no matter how much torque is sent to the motors, the sample will not move. In the real world, allowing increased torque to be continuously sent to the Z axis motor may result in breakage of the sample tube. Accordingly, it is desirable to stop sending current to the motor prior to the asymptotic artifact seen at time 138. Accordingly, embodiments may attempt to halt the motors at some time between time 136 and time 138.

An exemplary system looks for a first characteristic bump (e.g. signal artifact peaking at time 134) in the positional error or motor torque curve to detect the presence of a spring. This bump corresponds to the deviation caused by external resistance and the resulting response of the control system to apply extra force. For example, a given amount of force of resistance will cause a given number of millimeters of the deviation in the position error, depending on how the control system is configured. The bump caused by engagement of the holdings spring will vary in magnitude depending on the resistance force caused by that spring. For example, larger springs or larger tubes will cause a larger deviation in the position error.

Assuming the control loop is sensitive enough and controller has information about the geometry of the tube holder and tube (such as through a vision system or other identifying means that identifies the tube size and the type of tube holder at the target position), the system can create a model of the expected positional error caused by holding spring as the tube is inserted. For example, if we have a 16 mm tube, for a nominal spring in the tube holder will produce a predetermined amount to force, such as 200 gms of force. You can compare the observed positional deviation/force with the expected deviation and determine if there is an error based on the tube and tube holder types. The controller may see 200, 500, 1000 gms, or might not see anything. This can be used to get a picture of what might be happening and determine if there is an issue. For a given tube and holder geometry, the controller can be programmed, such as via machine learning or using predetermined values, to have an expected range for the initial position-error bump caused by the holding spring. This range can act as tolerances to assist the controller in determining whether the tube has entered the tube holder under nominal conditions, or whether an error is occurring. If the position error bump is out of tolerance, the system may adjust the trajectory to slow the descent of the tube down to mitigate further errors.

The controller may repeatedly see a spring force that deviates from the expected signal for all tubes and holders; this may indicate an issue in a vision system or calibration of the arm. The controller may repeatedly have the same problem in a particular cavity, which could indicate that maybe the cavity has a spring that is failing. In this way, position errors can assist in conflict diagnostics on the system, because the controller can capture this sort of information repeatedly. It is generally desirable to have a highly repeatable system to allow detection of anomaly. Repeatability allows the controller to continuously compare the observed interaction between the tube and the tube holder against the nominal profile. Ideally, a spring force should be roughly constant and repeatable. Recording the observed error signal for a given tube holder and viewing how it changes over multiple insertions can yield diagnostic information. Because the force for a given spring should be constant, if it abruptly changes, it can indicate that something is stuck in it or the spring has failed. You can also detect wear and drift in the instrument. In some embodiments, the controller can perform these comparisons in substantially real time and mathematically manipulate these signals from inside the control loop to quickly adapt.

In some embodiments, processor starts with a basic theoretical model of the geometry for a given the tube and the tube holder type, so that the processor has some predetermined expectation for where bumps in the error signal (e.g. the deviation when the tube encounters spring and the bottom) should be. A processor can also have a learning algorithm that, without necessarily having a pre-determined model, over time learns the expected relationship between XYZ and the position error signal (or other force-indicating signal). For example, with one type of tube and one type of tube holder the controller will tend to see the spring-force hump at a given location and the asymptotic error that indicates a bottom at another location. In addition, a processor can record historic events with individual tube holders to create a log of past tubes interacting with the tube holder. This log can show where there is a deviation for an individual tube holder from the model of all tube holders. This deviation may be sudden, indicating an error, or it could drift over time that indicates that the tube holder spring might be starting to wear out.

Logs can provide a wealth of information inside these control loops signals that can be mined for diagnostic purposes. If you have a good geometric understanding of what your system is and you have these signals, you can more fully understand what happens within the system.

There are a number of signals, including the position error that can be used to confirm placement and detect errors from existing signals in a servo-based system (or stepper based system). Many other signals can exist in the control loop. This can include velocity and accelerations signals that can be reported via an accelerometer sensor or derived from a position or other decoder. Signals can also include monitoring the current or load for a motor controller to determine that resistance has been encountered.

In some embodiments, sensors, such as accelerometers can be added to a tube placement device to supply additional information. This may allow, in addition to existing signals (such as motor load and position error) measurement of a state attribute that gives additional comparison information. In some embodiments, a processor verifying the proper placement of a tube can utilize the available position sensor to detect when a spring device has been engaged and a bottom has been encountered. In some embodiments, other signals, such as accelerometer signals, can be used to perform this analysis or to verify the detection of these tube receptacle features. In some embodiments, the position error signal is derived from an encoder and the mathematical manipulation of the encoded position (such as by comparing detected position to expected position). In some embodiments, a low cost accelerometer, such as miniature gyroscope type, can be used without adding much additional weight or cost. This can give you an external measure to confirm the behavior derived from position data or error signal.

In some embodiments, a processor focuses on the position error signal to detect when parts (e.g., spring device or bottom) of a tube receptacle have been encountered. In some embodiments a processor can use velocity or acceleration signals in a similar manner, to detect where a tube first encounters the spring and where it encounters the bottom in comparison to where the processor expects the tube to be.

A processor can focus its signal analysis on a region of interest. The region of interest can be chosen to create boundaries where the controller is most interested in confirming the placement of the tube. If the system is manipulating a tube inside of largely open space, the processor does need to focus on the position/error signal to confirm placement or to detect errors or features of the environment when not near objects in the environment. By defining a region of interest near the expected location of objects in the environment, the robot arm can move quickly in the open space without impediment by the processor. When moving in open space, processor overhead can be minimal and the velocity of the robot arm can be higher without affecting the real-time nature of the motor controller. In open spaces, there is generally no need to utilize the error signal to confirm placement, and traditional motor control algorithms can dictate manipulation of the motor driving robot arm. A region of interest creates a virtual region in space that allows the processor to identify when to carefully monitor the error signal. This region is generally around expected objects in the environment. For example, a region of interest can begin slightly above the expected top of a tube holder. That region may end after the expected bottom of the cavity of the tube holder, because it is unexpected that the tube would travel past this position.

The region of interest creates a virtual space by which the controller/processor monitors the error signal for artifacts related to the tub holder and creates another space outside the region of interest where the controller is less interest respect to confirming tube placement. The controller can use the error signal for other purposes, such a trajectory control and error detection, while outside the region of interest. The region of interest can create a mathematical boundary for enabling the search for specific signal attributes associated with salient features of the tube. This can increase processor efficiency and allow tubes to move more swiftly while outside the region of interest. The processor may not have to compute derivatives and other functions of the signal, which have extra processor overhead, because it is unlikely that the tube will encounter objects outside the region of interest.

Figure 4:
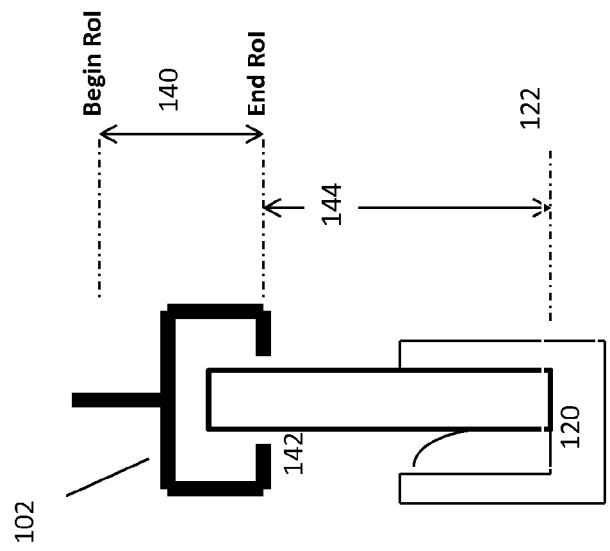
FIG. 4 is a cross sectional view of an exemplary region of interest with respect to a sample tube receptacle for use with some embodiments.

An exemplary region of interest is shown in FIG. 4. Region of interest 140 can be defined as the region in space where the position of a known point on the end effectors of the robot arm is of particular interest with respect to tube placement. Region of interest 140 can be identified by observing the geometry of end effectors 102 carrying tube 142 with respect to tube holder 120. By identifying the distance between the known point on the end effectors in the presumed bottom of the sample tube 142, the bottom of the region of interest can be identified with respect to the expected location of bottom 122 of tube holder 120. In this example, a distance 144 is determined to be an offset value between the location of bottom 122 and the expected corresponding location of the fixed point on the end effectors 102. It should be appreciated that distance 144 may be adjusted such that the endpoint of region of interest 140 can correspond to a location lower than bottom 122, allowing the error signal to be observed with past the expected bottom, to allow for tolerances and out-of-nominal conditions.

The region of interest can be defined by a beginning region of interest at the highest point where the end effectors should be when the bottom of the tube is within some threshold distance of the tube holder and a bottom where the end effectors are some threshold distance past where the tube should have bottomed out. If the signal indicates that the tube has encountered something before it enters the region of interest, the processor can either ignore it or, if large, it can note an error. Similarly, if the end effectors move past the end of the region of interest without detecting the bottom that means that something is wrong, such as the tube holder being out of place.

One way you could detect that the asymptotic property observed at the bottom of the tube holder receptacle is to determine the derivative of the position error. Along the curve of the position error signal, the curve is going to approach an asymptote (or appear exponential). A processor can use a derivative function to look for some rate of change in the error signal. Once the derivative surpasses a threshold value, it can indicate that a hard surface has been encountered and the controller can identify where to stop without breaking a sample tube. A small, un-sustained slope can indicate that something is compliant, such as a spring has been encountered. A small error and a small slope indicate that the tube can freely move.

FIG. 4 shows an exemplary system diagram for system that can be utilized with embodiments discussed throughout. A central processor or microcontroller 150 can carry out the logic for implementing embodiments. Microcontroller 150 sends physical motor control signals 152 to a power stage 164 for driving a motor 160. In some embodiments, motor 160 may be a brushless DC motor. Control signals 152 can include U, V, and W sinusoidal control signals suitable for controlling power stage 164, or any other suitable control signals. Motor 160 physically moves a sample handling arm, such as via the Z axis, which results in physical movement. Motor encoder 168 can track the physical movement of the control arm. This can include velocity or position encoding. Motor encoder 168 reports the encoded motion observed to microcontroller 150 via signals 154. Signals 154 may include pulse width modulated signals that are suitable for determining kinematic properties of motor 160, or any other suitable signals. Microcontroller 150 can use signals 154 to compare the observed physical motion of motor 162 the expected physical motion. This can result in a position or velocity error signal. Microcontroller 150 can use this error signal any of the manners discussed throughout.

Microcontroller 150 can include several hardware components executing software to carry out various steps. At step 170, microcontroller 150 determines and output response to send to power stage 164. This step can be accomplished using any motor control profiles or protocols as known in the art. At step 172, control signals are updated in response to the determination step 170. At step 174, and I/O device in microcontroller 150 generates motor control signals 152 for sending the power stage 164. At step 176, microcontroller 150 receives encoder signals 154. These signals are then used by a robot position estimation engine within microcontroller 150. The estimation engine can utilize pulse width modulated signals to count to determine approximate position, velocity, or other kinematic properties of motor 160. At step 178, microcontroller 150 compares the estimation of position generated by step 176 to determine whether or not the sample tube has moved into the region of interest, as well as a position error signal. Using this position error signal an indication whether the sample tube has entered the region of interest, the determination step 170 can proceed in accordance with the embodiments discussed throughout. For example, step 170 can include observing the position error signal for asymptotes when the sample tube is within the region of interest and stopping motor 160 accordingly. Step 170 can also be used to confirm placement.

Software running on a processor of the microcontroller generally performs the following steps. First a trajectory is determined that includes determining an expected location of features of the tube receptacle in the tube holder. Then, during motion of the sample tube, the microcontroller determines when the end effectors of the robot arm carrying the tube have entered a region of interest (and by extension when the bottom of the tube has entered its corresponding region—these can be considered equivalent calculations). Within this region of interest, the processor determines whether the tube has encountered a holding spring, by observing features in an error signal or required torque output sent to the motor. This can include calculating a derivative to determine that compliant resistance has been encountered. It should be noted that there are various electrical signals that can be considered for this determination.

Once the spring is detected, the processor can look for an exponential or asymptotic characteristic at a predetermined distance from the spring, which indicates the bottom of the tube receptacle. Finding an artifact in the error signal that has a derivative indicating exponential or asymptotic features at the expected location can verify proper placement of the sample tube. In response to these determinations, the controller, at the direction of its processor, can control the motor of the robot arm in substantially real time. As used herein, substantially real time indicates that calculations related to proper to placement occur rapidly enough to allow the results of these determinations to affect electrical signals sent to the motor for the robot arm placing the tube. For example, if features in the error signal indicate a problem, control signals that halt the motor can be sent. Furthermore, if the asymptotic features of a bottom of a tube receptacle are detected, the robot arm can be halted before the sample tube is damaged.

It should be understood that the electrical signals that are considered by the processor of the microcontroller can relate to position error, velocity error, acceleration error, motor load or current, etc. Using conventional motor control theory, the processor in the microcontroller can be configured to utilize the feedback of the electrical signal to determine an amount of power to be sent to the motor of the robot arm to maintain the intended trajectory of the sample handling robot arm.

Software executed by a processor in the microcontroller 150 can carry out any number steps to utilize the concepts disclosed herein. An exemplary method 180 is shown in FIG. 6. For example, at step 182, the processor of microcontroller 150 can receive at least one electrical signal (which can include any combination of the feedback signals discussed herein) relating to an operating condition of the sample handling device. For example, the electrical signal may be an error signal that relates to the position of the sample handling device relative to an expected trajectory. Similarly, velocity and acceleration or motor load can be considered. At step 184, microcontroller 150 sends signals that move a sample tube via the sample handling device to a region of interest in space that is near the expected location of a tube receptacle of a tube holder. At step 186, microcontroller 150 determines the expected location of the tube receptacle, as well as the important features of the tube receptacle, such as holding springs and the bottom of the receptacle. It should be appreciated, that microcontroller 150 maintains a model of the environment that includes, for instance, the expected location of the bottom of the sample tube being carried by the sample handling device.

Once microcontroller 150 has a model for the environment and has determined based on position encoding or other means that the sample tube and handling device have entered the region of interest, microcontroller 150 can look for salient features in the electrical signal to determine whether placement is occurring as expected. At step 188, microcontroller 150 determines from the electrical signal, such as by observing a derivative, that the tube has encountered a spring device in the tube receptacle. This information can be used to establish bounds for the expected location of the bottom of the tube receptacle. At step 190, microcontroller 150 subsequently determines from the electrical signal that the bottom of the tube has encountered the bottom of the tube receptacle to verify placement of the sample tube. As discussed throughout, this determination can be based on the presence of an asymptotic or exponential error or load. At step 192, microcontroller 150 responsively controls the sample handling device in substantially real time based on the previous steps. For example, if the error indicates that the bottom has been located, the microcontroller issues halt instructions, cutting power to the motor driving a sample handling device before a threshold amount of force is applied to the sample tube, which could cause damage.

Embodiments may also be used with a tray vision system, such as that described in US Publication No. 2012P23220US, which is herein incorporated by reference. As discussed in that application, a system can use different tubes of different sizes and can also use different sample tube holder geometries. Tube receptacles can include the tube holders in trays or in carriers, such as passive pucks or those described in PCT Publication No. 2011P24306WO, which is herein incorporated by reference. These carriers can be configured to traverse an automation system, allowing a tube placement device, such as a robot arm, to place tubes using any of the methods described herein into tube receptacles for storage or to allow the tubes to be shuttled anywhere within the automation system. These concepts may also be used in some present embodiments.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A system for placing sample tubes into tube receptacles, comprising:

a sample handling device configured to position a sample tube and to provide at least one electrical signal relating to an operating condition of the sample handling device;

at least one tube receptacle configured to receive the sample tube from the sample handling device, the at least one tube receptacle comprising a bottom and at least one spring device configured to apply a holding force to the sample tube when placed in the tube receptacle; and at least one processor configured to control the sample handling device and receive the at least one electrical signal, wherein the at least one processor is configured to:

determine an expected location of the tube receptacle, determine, during placement of the sample tube, from the at least one electrical signal, that the tube has encountered the spring device, subsequently determine from the at least one electrical signal that the tube has encountered the bottom of the tube receptacle, to verify proper placement of the sample tube, and control the motion of the sample handling device in substantially real time, in response.

2. The system of claim 1, wherein the sample handling device includes at least one servo motor.

3. The system of claim 1, wherein the at least one electrical signal indicates a deviation of at least one of an acceleration, a velocity, and a position, from an expected trajectory of the sample handling device.

4. The system of claim 1, wherein the sample handling device includes at least one motor and the at least one electrical signal relates to a load experienced by the motor.

5. The system of claim 1, wherein the sample handling device comprises a robot arm.

6. The system of claim 1, wherein the at least one tube receptacle is part of a tray for carrying multiple sample tubes.

7. The system of claim 1, wherein the at least one tube receptacle is part of a carrier configured to move around an automation track in an analyzer.

8. The system of claim 1, further comprising a controller configured to utilize the at least one electrical signal to determine an amount of power to use to maintain a trajectory of the sample handling device.

9. A placement device for use in an IVD environment, comprising:
a sample handling device configured to position a sample tube and to provide at least one electrical signal relating to an operating condition of the sample handling device;
at least one processor configured to control the sample handling device and receive the at least one electrical signal, wherein the at least one processor is configured to:
determine an expected location of a tube receptacle,
determine, during placement of the sample tube, from the at least one electrical signal, that the tube has encountered a spring device in the tube receptacle,
subsequently determine from the at least one electrical signal that the tube has encountered a bottom of the tube receptacle, to verify proper placement of the sample tube in the tube receptacle, and
controlling the motion of the sample handling device in substantially real time, in response.

10. The placement device of claim 9, wherein the sample handling device includes at least one servo motor.

11. The placement device of claim 9, wherein the at least one electrical signal indicates a deviation of at least one of an acceleration, a velocity, and a position, from an expected trajectory of the sample handling device.

12. The placement device of claim 9, wherein the sample handling device includes at least one motor and the at least one electrical signal relates to a load experienced by the motor.

13. The placement device of claim 9, wherein the sample handling device comprises a robot arm.

14. The placement device of claim 9, further comprising a controller configured to utilize the at least one electrical signal to determine an amount of power to use to maintain a trajectory of the sample handling device.

15. The placement device of claim 9, wherein at least one processor further determines a region of interest that includes a portion of a trajectory of the sample tube that includes the expected location of the spring device and the bottom of the tube receptacle.

16. A method of placing sample tubes into tube receptacles, comprising steps of:
receiving, at a processor, at least one electrical signal relating to an operating condition of a sample handling device;
moving a sample tube via the sample handling device to a region of interest near a tube receptacle;
determining an expected location of the tube receptacle;
determining, during placement of the sample tube, from the at least one electrical signal, that the tube has encountered a spring device in the tube receptacle;
subsequently determining from the at least one electrical signal that the tube has encountered a bottom of the tube receptacle, to verify proper placement of the sample tube in the tube receptacle; and
controlling the motion of the sample handling device in substantially real time, in response.

17. The method of claim 16, wherein the sample handling device includes at least one servo motor.

18. The method of claim 16, wherein the at least one electrical signal indicates a deviation of at least one of an acceleration, a velocity, or a position, from an expected trajectory of the sample handling device.

19. The method of claim 16, wherein the sample handling device includes at least one motor and the at least one electrical signal relates to a load experienced by the motor.

20. The method of claim 16, wherein the at least one tube receptacle is part of a tray for carrying multiple sample tubes.

21. The method of claim 16, wherein the at least one tube receptacle is part of a carrier configured to move around an automation track in an analyzer.

22. The method of claim 16, wherein the step of moving the sample tube comprises utilizing the at least one electrical signal to determine an amount of power to use to maintain a trajectory of the sample handling device.

* * * * *